(12) United States Patent
McGaffigan et al.

(10) Patent No.: US 9,814,515 B2
(45) Date of Patent: Nov. 14, 2017

(54) LAPAROSCOPIC MEDICAL DEVICE WITH DE-MATEABLE TIP

(75) Inventors: Thomas Haynes McGaffigan, Saratoga, CA (US); Sharad H. Joshi, Hopkinton, MA (US)

(73) Assignee: MICROLINE SURGICAL, INC., Beverly, MA (US)

( * ) Notice: Subject to any disclaimer, the term of this patent is extended or adjusted under 35 U.S.C. 154(b) by 1145 days.

(21) Appl. No.: 13/250,046

(22) Filed: Sep. 30, 2011

(65) Prior Publication Data
US 2012/0083778 A1    Apr. 5, 2012

Related U.S. Application Data

(60) Provisional application No. 61/388,655, filed on Oct. 1, 2010.

(51) Int. Cl.
| | | |
|---|---|---|
| *A61B 18/04* | (2006.01) | |
| *A61B 18/18* | (2006.01) | |
| *A61B 18/14* | (2006.01) | |
| *A61B 18/08* | (2006.01) | |
| *A61B 17/29* | (2006.01) | |
| *A61B 17/00* | (2006.01) | |

(52) U.S. Cl.
CPC ........ *A61B 18/1445* (2013.01); *A61B 18/085* (2013.01); *A61B 17/29* (2013.01); *A61B 2017/0046* (2013.01); *A61B 2017/00473* (2013.01); *A61B 2017/294* (2013.01)

(58) Field of Classification Search
CPC .............. A61B 18/085; A61B 18/1445; A61B 2017/294; A61B 2017/0046; A61B 2017/00473; A61B 2017/2931; A61B 17/29

USPC .......................................................... 606/28
See application file for complete search history.

(56) References Cited

U.S. PATENT DOCUMENTS 5,172,700 A * 12/1992 Bencini .................. A61B 10/06
                                                                    600/564
5,324,297 A *  6/1994 Hood .................. F16L 37/2445
                                                                    604/22
(Continued)

FOREIGN PATENT DOCUMENTS

DE    102008051866    1/2010
JP    5-212046        8/1993
(Continued)

OTHER PUBLICATIONS

Search report from E.P.O., dated Jan. 14, 2015.
(Continued)

*Primary Examiner* — Christopher D Koharski
*Assistant Examiner* — Pamela M Bays
(74) *Attorney, Agent, or Firm* — Greenblum & Bernstein, P.L.C.

(57) ABSTRACT

A laparoscopic instrument assembly with a handle member and a removable tip. The handle member and removable tip are mated using a double threaded design which provides a secure connection with low electrical resistance. Electrical energy is provided through an inner shaft to the removable tip, and a return energy path is formed using an outer tubing of the instrument assembly. The removal tip includes a cutting and sealing device with a resistive member that is provided with the electrical energy, thereby enabling the tip to cut and seal tissue.

10 Claims, 5 Drawing Sheets

(56) References Cited

U.S. PATENT DOCUMENTS

| | | | |
|---|---|---|---|
| 5,358,508 A * | 10/1994 | Cobb et al. | 606/174 |
| 5,439,478 A * | 8/1995 | Palmer | A61B 1/00087 |
| | | | 600/564 |
| 5,551,448 A | 9/1996 | Matula et al. | |
| 5,562,640 A | 10/1996 | McCabe et al. | |
| 5,628,760 A | 5/1997 | Knoepfler | |
| 5,752,951 A | 5/1998 | Yanik | |
| 5,810,879 A * | 9/1998 | de Guillebon | 606/205 |
| 6,039,734 A * | 3/2000 | Goble | A61B 18/12 |
| | | | 606/41 |
| 6,406,470 B1 | 6/2002 | Kierce | |
| 6,409,728 B1 | 6/2002 | Ehr et al. | |
| 6,595,984 B1 | 7/2003 | DeGuillebon | |
| 6,689,071 B2 * | 2/2004 | Burbank | A61B 10/0266 |
| | | | 600/564 |
| 6,730,081 B1 * | 5/2004 | Desai | A61B 17/00234 |
| | | | 604/8 |
| 2005/0033354 A1 * | 2/2005 | Montalvo | A61B 10/06 |
| | | | 606/205 |
| 2005/0131396 A1 * | 6/2005 | Stanczak et al. | 606/1 |
| 2007/0088351 A1 | 4/2007 | Ewaschuk et al. | |
| 2008/0004656 A1 | 1/2008 | Livneh | |
| 2008/0243106 A1 * | 10/2008 | Coe et al. | 606/1 |
| 2009/0062726 A1 * | 3/2009 | Ford | A61B 17/12022 |
| | | | 604/57 |
| 2009/0198224 A1 | 8/2009 | McGaffigan | |
| 2009/0240274 A1 | 9/2009 | Boebel et al. | |

FOREIGN PATENT DOCUMENTS

| | | |
|---|---|---|
| JP | 2009-226213 | 10/2009 |
| WO | 2008/005433 | 1/2008 |

OTHER PUBLICATIONS

Japanese Office Action, dated May 27, 2014, in corresponding Japanese Patent Application No. 2013-141208, along with an English translation thereof.

Canada Office action, dated Dec. 13, 2012.

Japan Office action, dated Apr. 2, 2013.

* cited by examiner

RELATED ART
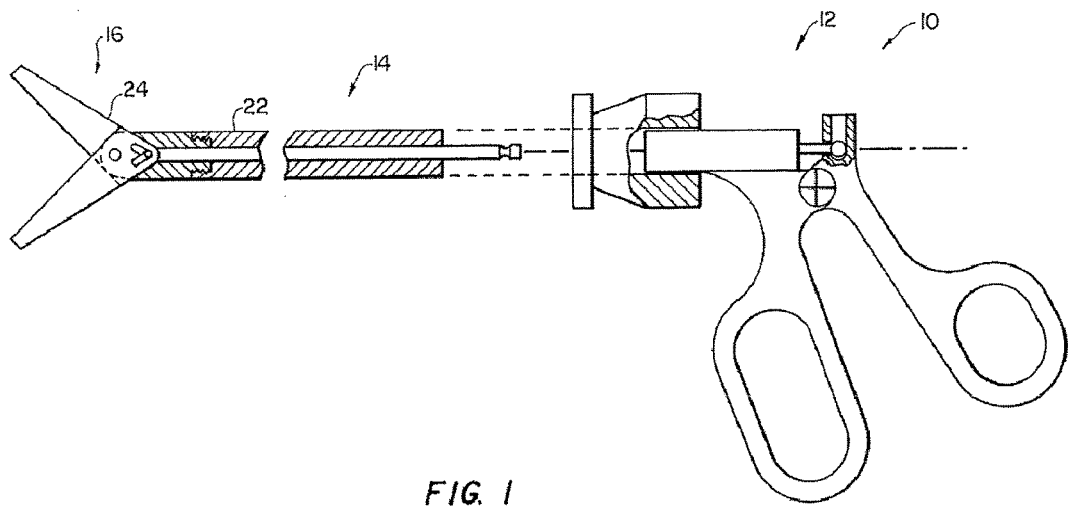
FIG. 1
FIG. 2
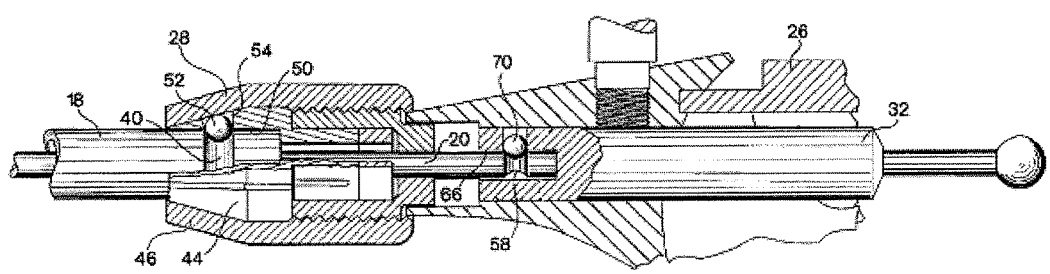
RELATED ART

RELATED ART

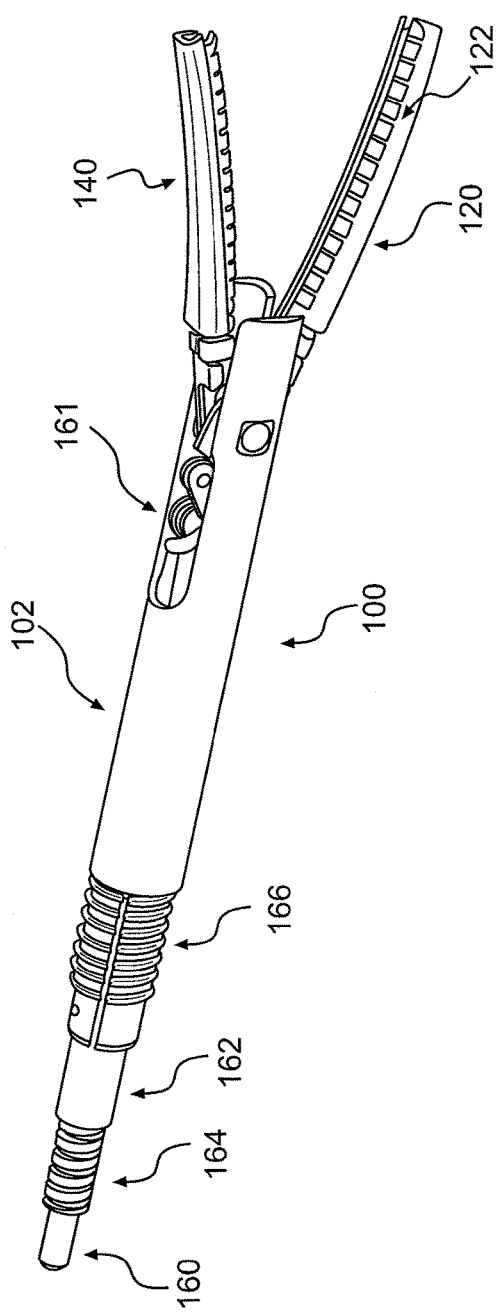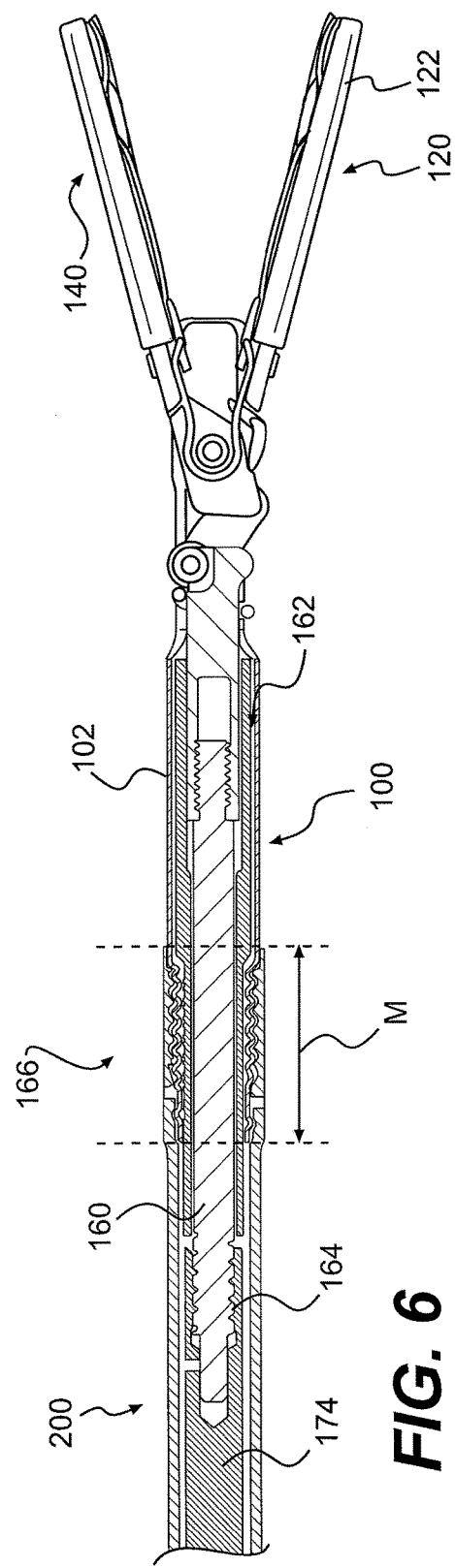

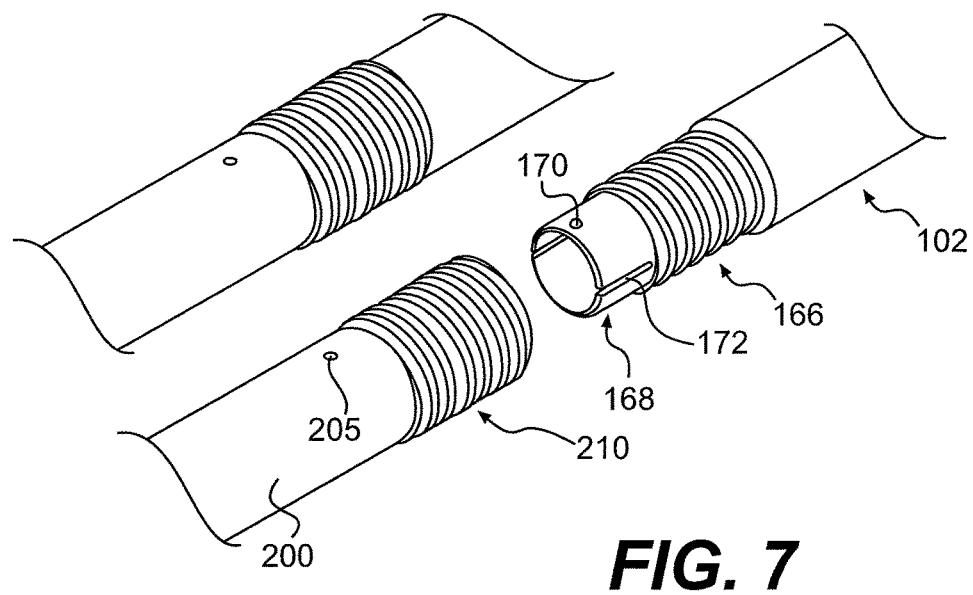
FIG. 7
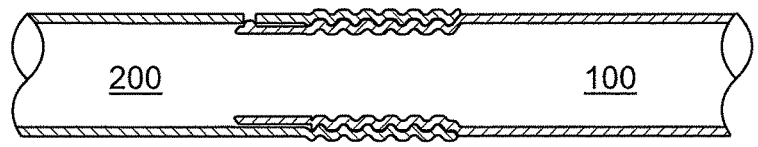
(A)
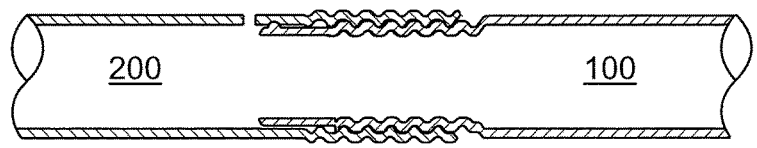
(B)
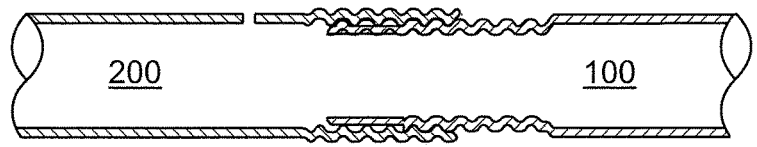
(C)
FIG. 8

LAPAROSCOPIC MEDICAL DEVICE WITH DE-MATEABLE TIP

CLAIM FOR PRIORITY

This application claims the benefit of priority to U.S. Provisional Application No. 61/388,655, field Oct. 1, 2010, the contents of which are expressly hereby incorporated by reference.

BACKGROUND

1. Field of the Invention

This invention relates to a laparoscopic instrument assembly having a removable tip, and in particular, having a removable tip provided with a double threaded design and an electrical return path.

2. Background of the Invention

Medical procedures such as laparoscopy and the like, which employ a tip at the end of a tube for insertion into the patient, are beneficial because the incisions necessary to perform them are minimal in size, therefore promoting more rapid recovery and lower costs. For example, a patient who undergoes laparoscopic surgery may typically return to normal activity within a period of a few days to about a week, in contrast to more invasive procedures requiring a relatively larger incision (which may require about a month for recovery). (Although the term "laparoscopic" is typically used hereinafter, such use of the term "laparoscopic" should be understood to encompass any such similar or related procedures such as, for example, arthroscopic, endoscopic, pelvoscopic and/or thoroscopic or the like, in which relatively small incisions are used.)

Current surgical devices are designed to function with mechanically operated tips. In other words, the design of a threaded tip and shaft assembly is specifically designed to mechanically attach a tip and also be able to transfer a force to the tip. Some existing laparoscopic devices use a screw-type threaded interface that does not provide low electrical resistances across the interface unless both the inner and outer thread forms are screwed together very tightly. However, it is difficult to build two or more coaxial thread forms that can be simultaneously mated and tightly fit together. Since tolerances and machining inaccuracies occur, one of the two threaded assemblies will always be tighter than the other, resulting in energy losses across the interface.

FIG. 1 shows a laparoscopic instrument assembly in accordance with the related art. Assembly 10 includes handle member 12 and shaft 14 operably interconnecting handle member 12 and removable tip 16. Removable tip 16 may be provided as part of assembly 10 or obtained separately. Distal end 22 of the shaft 14 is operably connected to tip 16 for actuation of surgical device 24 on tip 16.

FIG. 2 shows a shaft a body of a laparoscopic assembly in accordance with the related art. Sheath 18 is held in conventional manner within casing 26 using collet 44. Additional securing mechanisms, such as a detent, are provided to ensure that sheath 18 is tightly secured within the body. When collet closer 28 is tightened about collet 44, detent member 52 is forced inwardly by the internal surface of collet closer conical portion 46, partially enters collet axial bore 50, and engages sheath groove 40 to hold sheath 18 firmly within the body. The number of detent members 52 and bores 54 is selected to optimize the gripping power of the detent members on sheath 18. At least one radial bore 68 is also formed in rod 32 to extend from the outer surface of rod 32 into and open to axial bore 66. Each radial bore 68 contains a detent member 70 therein for mating engagement of detent member 70 with groove 58. The number of detent members 70 is selected to optimize the gripping power of the detent members on rod 20. Each detent member 70 engages groove 58 during actuation of surgical tip device, preventing removal of rod 20 from axial bore 66. However, sheath 18 may be released from casing 26 as described above, and detent members 70 may be disengaged from groove 58.

FIG. 3 shows an instrument tip and actuator assembly in accordance with the related art. At the rear of the casing structure 24, a yoke 26 is located having an external thread 25 formed on the rear end thereof. In addition to the continuous thread 25 formed on the yoke 26, the operable tip 14 is provided with a continuous internal thread (not shown) formed on the inner surface of the tip casing structure 24. The actuator 12 includes an outer sheath 36, having an insert which may be press fit into the sheath 36, with a continuous external thread 39 formed at its forward end, the thread 39 being of matching pitch and diameter to the internal thread provided on the operable tip 14. The thread 25 is configured to threadedly mate with internal threading of an actuation rod (not shown) slidably positioned within the sheath 36 such that sliding movement of the actuation rod operates the tip.

FIG. 4 shows an exemplary embodiment of a cutting and sealing device of a laparoscopic instrument assembly in accordance with the related art. US Publication No. 2009/0198224, the entire contents of which are hereby incorporated by reference, discloses a tissue cutting and sealing device provided on the distal end of an endoscopic device 10. A pair of opposing jaws 20 and 40 dimensioned to grasp tissue therebetween is also provided, and a heating assembly 22 is provided on jaw 20. Heating assembly 22 includes a ceramic body 24 with a metalized portion 26 extending along a top surface of ceramic body 24. The heater assembly 22 provides a resistive heating element 26 on top and integral with the ceramic substrate 24. The design is advantageous since the temperatures in ceramic body 24 are always lower than the temperatures in the metalized portion 26. In addition, the ceramic acts as a heat spreader that increases the effective seal area of the heater. The design promotes tissue sealing adjacent to the ceramic and tissue cutting adjacent to the metalized portion.

SUMMARY OF THE INVENTION

A laparoscopic instrument assembly with a handle member and a removable tip. The handle member and removable tip are mated using a double threaded design which provides a secure connection with low electrical resistance. Electrical energy is provided through an inner shaft to the removable tip, and a return energy path is formed using an outer tubing of the instrument assembly. The removal tip includes a cutting and sealing device with a resistive member that is provided with the electrical energy, thereby enabling the tip to cut and seal tissue.

In one embodiment, A laparoscopic device includes a removable tip having an electrically-conductive first outermost casing with an electrical energy path; and a handle member for removably receiving and actuating the removable tip.

In one aspect, the removable tip further comprises a first inner shaft with a first threaded member, and the first outermost casing has a second threaded member, the first and second threaded members having different thread forms.

In another aspect, the handle member has a second inner shaft with a third threaded member mateable with the first threaded member, and the handle member has a second outermost casing with a fourth threaded member mateable with the second threaded member.

In still another aspect, the first outermost casing of the removable tip has a detent, and the second outermost casing of the handle member has a detent hole for removably receiving the detent.

In yet another aspect, the first outermost casing of the removable tip is spring biased at the second threaded member end.

In another aspect, the device includes an inner shaft assembly configured to transfer electrical energy from a power source to the removable tip, the inner shaft assembly comprising the first inner shaft of the removable tip mated with the second inner shaft of the handle member.

In still another aspect, the device includes a cutting and sealing device at a distal end of the removable tip with at least one resistive heating member activated by the electrical energy delivered from the inner shaft assembly and returned via the electrical energy path.

In yet another aspect, the first threaded member has a helix angle different from a helix angle of the second threaded member.

In another aspect, the device includes insulation located between the first inner shaft and the first outermost casing of the removable tip, which insulation extends along at least a portion of the length of the first outermost casing.

In still another aspect, the second threaded member comprises a set of threads extending to both inner and outer sides of first outermost casing.

In another aspect, a pitch of the inner and outer threads of the first threaded member and the second threaded member are the same.

In another embodiment, there is a removable tip for a laparoscopic device including an electrically-conductive outermost casing with a first threaded member and configured as an electrical energy path; and an inner shaft located at least partially within the outermost casing and having an second threaded member.

In one aspect, the first threaded member and the second threaded member are different thread forms and configured to mate with complementing threaded members.

In another aspect, the tip includes a cutting and sealing instrument at an end of the removable tip opposite of the second threaded member and including at least one resistive heating member.

In still another aspect, electrical energy is provided to and traversed along a path of the inner shaft of the removable tip, and the electrical energy returns along the electrical energy path defined by the outer host casing.

In yet another aspect, the at least one resistive heating member is activated when provided with the electrical energy.

In another aspect, the outermost casing has a detent and is spring biased at the first threaded member end.

In still another aspect, the first threaded member has a helix angle different from a helix angle of the second threaded member.

In yet another aspect, the tip includes insulation located between the inner shaft and the outermost casing, which insulation extends along at least a portion of the length of the outermost casing.

In another aspect, the second threaded member comprises a set of threads extending to both inner and outer sides of first outermost casing.

In still another aspect, the first threaded member has a helix angle greater than a helix angle of the second threaded member.

In yet another aspect, the removable tip further comprises a first inner shaft with a connector configured to removably connect to a second inner shaft of the handle member, and the first outermost casing has outermost casing threading configured to removably threadedly connect to a second outer casing of the handle member.

In another aspect, a pitch of the inner and outer threads of the first threaded member and the second threaded member are the same.

Other exemplary embodiments and advantages of the present invention may be ascertained by reviewing the present disclosure and the accompanying drawings, and the above description should not be considered to limit the scope of the present invention.

BRIEF DESCRIPTION OF THE DRAWINGS

The present invention is further described in the detailed description which follows, in reference to the noted plurality of drawings, by way of non-limiting examples of preferred embodiments of the present invention, in which like characters represent like elements throughout the several views of the drawings, and wherein:

FIG. 1 shows a partial cross sectional view of laparoscopic an instrument assembly in accordance with the related art.

FIG. 2 shows a cross sectional view of a portion of a shaft a body of a laparoscopic assembly in accordance with the related art.

FIG. 5 shows an exemplary embodiment of a removable tip with a cutting and sealing device in accordance with the present invention.

FIG. 6 shows an exemplary cross-sectional view of the removable tip illustrated in FIG. 5 in accordance with the present invention.

FIG. 7 shows an exemplary embodiment of the outer tubing of the removable tip and handle member in accordance with the present invention.

FIG. 8 shows another exemplary embodiment of the outer tubing of the removable tip and handle member in accordance with the present invention.

DETAILED DESCRIPTION

Figure 3:
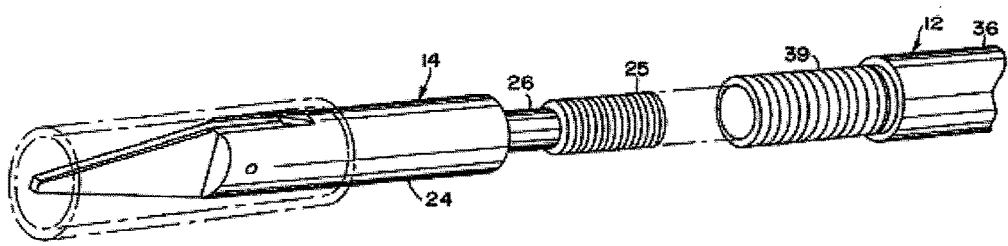
FIG. 3 shows an instrument tip and actuator assembly in accordance with the related art.
Figure 4:
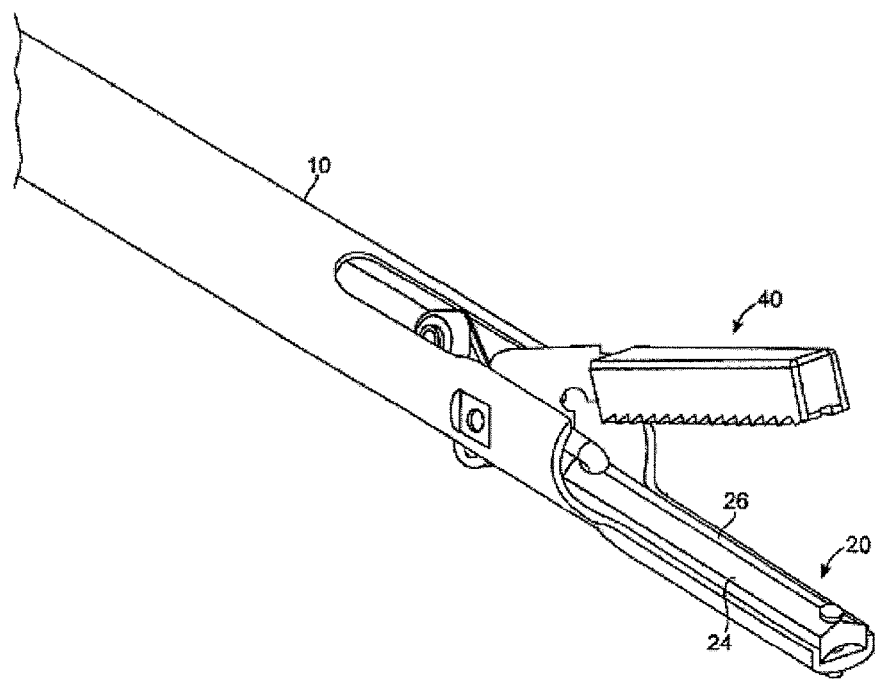
FIG. 4 shows an exemplary embodiment of a removable tip with a cutting and sealing device of a laparoscopic instrument assembly in accordance with related art.

The particulars shown herein are by way of example and for purposes of illustrative discussion of the embodiments of the present invention only, and are presented for providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

Referring to the drawings wherein like characters represent like elements, FIG. 5 shows an exemplary embodiment of a removable tip with a cutting and sealing device in accordance with a non-limiting aspect of the present disclosure. Removable tip 100 includes, for example, outer casing or tubing 102 with threaded member 166, and an inner shaft 160 which has threaded member 164. The outer tubing 102 and the inner shaft are preferably made of metal or other electrically-conductive material. Insulation 162 is provided between inner shaft 160 and outer tubing 102 to prevent electrical contact therebetween, as explained below. A cutting and sealing device is attached at the distal end of the removable tip 100, and includes jaws 120 and 140 and heating member 122. Although depicted as a single heating member, heating member 122 may be provided on jaw 120, jaw 140 or both jaws 120 and 140. Moreover, more than one heating member 122 may be located on any one jaw. The removable tip 100 is designed to provide mechanical attachment to a handle member (not shown), as well as receive and transfer mechanical force and energy, such as electrical, mechanical (e.g., vibration, oscillatory, etc.), electromechanical and/or kinetic energy. For example, a power source (typically 9 volts, although those skilled in the art would understand that the voltage may be any suitable voltage as an alternative to 9 volts) provides energy to the handle member connected to the removable tip 100. The removable tip 100 receives the supplied energy and delivers the energy to heating member 122, thereby heating the heating member 122 to the desired temperature (explained below in more detail). In conjunction with the cutting and sealing device attached to the removable tip 100, the heating member enables cutting and sealing of tissue. That is, the removable tip 100 can cut and seal tissue during surgical procedures at the same time. It is noted that no electrical current passes through the tissue being grasped by the cutting and sealing device in order to perform the procedure. Hence, no electrosurgical procedure occurs.

The supply of energy to the laparoscopic device is now described. Energy (in the form of electrical current) is transferred from a power source (not shown) to the cutting and sealing device of the removable tip 100 through the shaft 160 (and inner shaft 174 of the handle member 200) and wire 161 (connecting the shaft to the cutting and sealing device). Alternatively, energy may be transferred by an internal wire running the length of the shaft 160 within the outer tubing 102. The energy is delivered to the heating member 122 of the upper and/or lower jaws 120 and 140 of the cutting and sealing device, thereby causing the heating member 122 to heat to the desired temperature. The heating element 122 therefore provides a resistive (i.e., ohmic) heating element with the cutting and sealing device. Once the supplied current passes through the heating element, it is returned to the power source to complete the circuit using the outer tubing 102 of the removable tip 100 as a return path, and ultimately along the outer casing of the handle member (not shown). In order to prevent the inner shaft 160 and outer tubing 102 from having electrical contact, insulation 162 is provided therebetween along at least a portion of the length of the outer tubing 102.

FIG. 6 shows an exemplary cross-sectional view of the removable tip illustrated in FIG. 5 in accordance with the present invention. Removable tip 100 includes, for example, outer tubing 102 with threaded member 166, inner shaft 164 with threaded member 160, and insulation 162 provided in between inner shaft 164 and outer tubing 102. As explained, the insulation 162 extends along at least a portion of the length of the outer tubing 102. Also included at the distal end of the removable tip 100 is a cutting and sealing device including jaws 120 and 140 and a heating member 122. As explained, heating member 122 may be provided on jaw 120, jaw 140 or any combination thereof. Moreover, more than one heating member 122 may be provided on any one jaw. The threaded members 164 and 166 may have different threaded forms. For example, the threads on threaded member 166 of outer tubing 102 may have a different pitch or thread form than the threads on threaded member 164 of inner shaft 160. More specifically, in one exemplary embodiment, an Edison type thread may be used as the threaded member 166 on the outer tubing 102 in combination with a high helix angle thread used as the threaded member 164 provided on shaft 160 of the removable tip 100. In other words, the high helix angle thread of the threaded member 164 has a thread helix angle higher than the helix angle of the threaded member 166, which allows the same pitch to be used on the inner and outer portions of the tip and equal travel with each revolution when connecting the tip 100 to the handle member 200. If the inner high helix thread is instead located on the outer tube 102, then the opposite holds true. One advantage of having a high helix thread angle is that there is a greater contact area between mated surfaces, thereby providing low electrical resistance, thus insuring little or no unwanted heat is generated at the connection.

The Edison thread allows the thread to be formed directly on the outer tube 102 (by pressing, crimping, embossing and the like) (and connecting handle member 200), thus reducing cost, increasing reliability and making a small profile. In other words, the threads of the Edison thread extend to both the inner and outer sides of the outer tubing 102. The Edison thread form is also rugged and provides a high level of force and energy transfer. In particular, when transferring electrical energy across the inner shaft assembly (the inner shaft of the handle member mated with the inner shaft of the removable tip), a mated surface area M results in low electrical resistance, thus insuring little or no unwanted heat is generated at the connection. The high helix thread of the inner shaft assembly, on the other hand, allows the inner shaft 160 and outer tube 102 to be mated to the handle member 200 (at respective inner shaft and outer tubing sections) at the same or differing rates (pitches) depending on the desired result. Different threads, pitches, etc. can be selected based on the length of the inner shaft in relation to the outer tube.

FIG. 7 shows an exemplary embodiment of the outer tubing of the removable tip and handle member in accordance with the present invention. A coaxial electromechanical threaded type connection system is used to connect the handle member with the removable tip. As illustrated, outer tubing 102 of the removable tip has a threaded member 166, such as an Edison thread, formed directly (i.e. integrated with or unitary to) on the outer tube 102. The integral thread design lowers part cost, increases reliability, lowers assembly time and is rugged. The integral threaded members 166 and 210 can be designed to be the outer tubing on the removable tip of handle member 200, or any combination thereof. The outer tube 102 may include a spring biased interface 168 in the form of one or more open channels 172, thereby allowing the proximal end of the outer tube to flex in the radial direction such that when the tip 100 is attached to the handle member 200, the outer tubing is slightly compressed and the spring action of the spring biased interface 168 biases the outer tubing radially outward against the handle member 200. While the figures show two open channels 172, it is understood by those skilled in the art that a single channel or three or more channels may be used, although it is preferred that when even number of channels are used, they be evenly spaced about the circumference of the outer tube.

As illustrated for example in steps (A), (B) and (C) of FIG. 8, the threaded member 166 can be continuous or include a series or array of bumps, bosses or extrusions that are aligned in a helix but are not connected together to from a continuous thread form. Both the male (166) and female (210) mating elements can utilize a continuous or discontinuous thread. A discontinuous thread form (for example, a series of bumps aligned in a helix) can be advantageous for manufacturing reasons or for other reasons. A continuous thread form may be produced by rolling the thread into the tube or by stamping the thread form into a flat sheet and then rolling the sheet into a tube form, or by any other suitable method. The tube form can then be welded or otherwise held together. It is appreciated that these are merely exemplary embodiments, and the invention is not limited to these examples.

Figure 9:
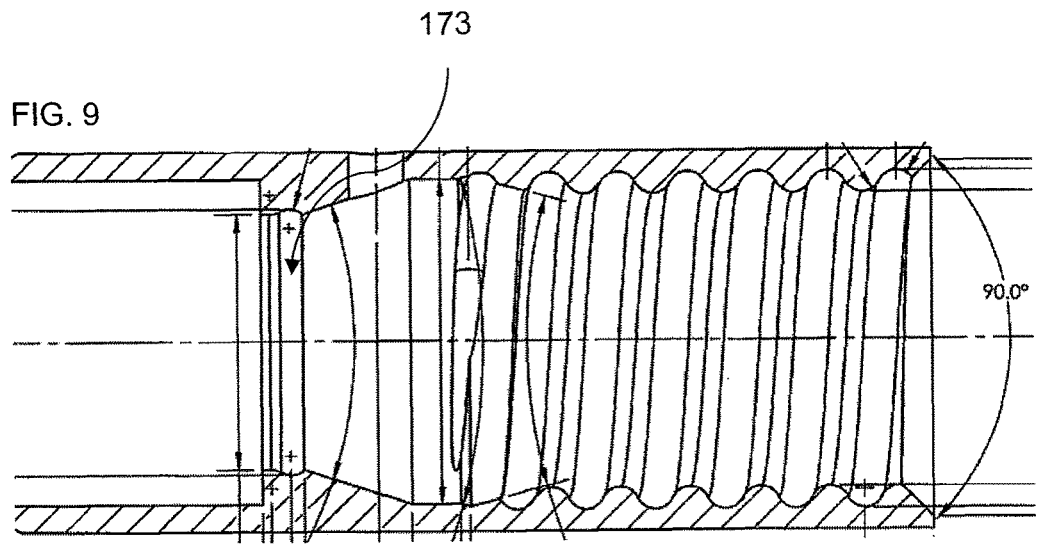
FIG. 9 shows another exemplary embodiment of the outer tubing of the removable tip and handle member in accordance with the present invention.
Figure 10:
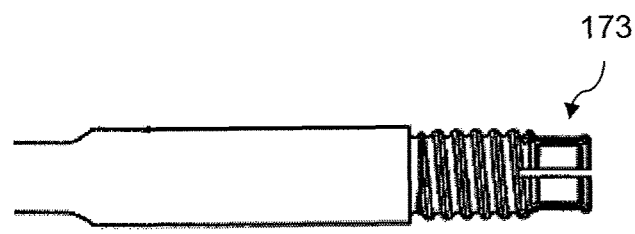
FIG. 10 shows another exemplary embodiment of the outer tubing of the removable tip and handle member in accordance with the present invention.
Figure 11:
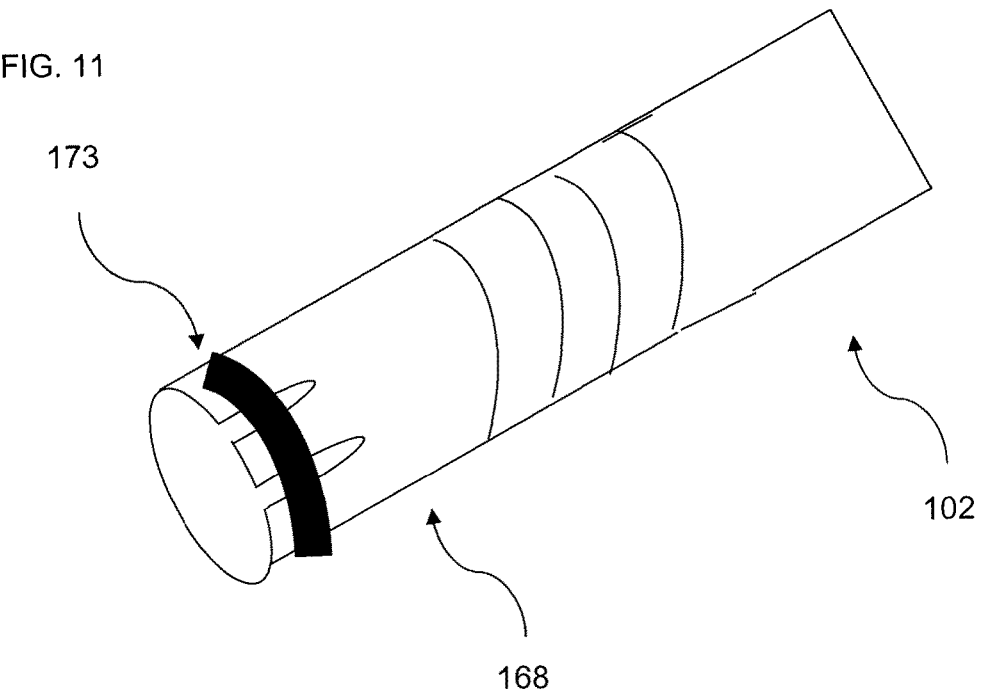
FIG. 11 shows another exemplary embodiment of the outer tubing of the removable tip and handle member in accordance with the present invention.

In one embodiment, a detent (in the form of, e.g., a boss) 170 can also be incorporated into the outer tube of outer tubing 102 in order to indicate that the removable tip 100 has been fully secured to the handle member 200. The detent 170 also improves the integrity of the connection and prevents unwanted unscrewing or overscrewing of the tip 100. The detent 170 can be as simple as a dimple on the tube, aligning itself and snapping into a detent hole 205 formed on the outer tube of the handle member 200. Alternatively, the detent 170 may be replaced or formed in conjunction with an annular ring 173 which circumferentially surrounds all of or portions of spring biased interface 168, as illustrated in FIGS. 9-11. Also, as described above, the spring biased interface 168 further biases the detent 170 into the detent hole when the tip 100 is attached to the handle member 200. As illustrated for example in steps (A), (B) and (C) of FIG. 8, the detent 170 is axially spaced along the outer tube 102 such that the detent is threaded through the threaded members 210 during attachment of the tip 100 to the handle member 200 and before engaging the detent hole 205. Alternatively or additionally, a detent 170 may be present on the handle member 200, and a detent hole 205 may be present on the outer tube 102. Although a detent 170 in the form of a boss is shown, it is understood by those of skill in the art that the detent may include more than one boss, or may take the form of an extruded ring or fluted portion, which, in such a situation, the detent hole 205 would be correspondingly formed to accommodate the form of the detent 170. Further, the detent hole 205 may or may not penetrate through the handle member. As understood, one or more detents may be used.

In other embodiments, the outer tube assembly (the outer tube of the handle member mated with the outer tube of the removable tip) has inner and outer formed threads with a 1 mm pitch on respective ends of the handle member and removable tip. The outer tubing 102 of removable tip 100 has externally formed threads and an integral detent (bump) 170 feature. The outer tubing of handle member 200 has internally formed threads and detent hole 205 that mates with detent 170. The shaft assembly (the inner shaft of the handle member mated with the inner shaft of the removable tip) has inner and outer formed threads with a 1 mm pitch. The inner shaft of handle member 200 has internally formed threads integrated into a single cantilever beam spring contact element and aligning feature for the external thread of inner shaft 160 of removable tip 100. Inner shaft 160 has, for example, a machined 1 mm pitch thread 164. Threaded member 164 of inner shaft 160 is threadedly inserted into the internal threaded shaft 174 (second inner shaft) of the handle member 200 in order to provide bending stiffness to the mated assembly. The shaft 174 may be electrically-conductive and in the form of an actuation rod that slidably translates within the handle member 200 (by actuation of, e.g., a trigger) to actuate the jaws 120, 140, although those skilled in the art would appreciate embodiments having no movable tip, such as a scraper and the like. In such embodiments, the shaft 174 does not translate. Those skilled in the art would appreciate that in alternative embodiments, rather than the inner shaft 160 being threadedly attachable to the shaft 174, the inner shaft may be attached to the shaft 174 by any suitable means of attachment, including but not limited to ball-and-clevis attachments, snap-fit attachments, spring-loaded ball-and-detent attachments and the like. It is appreciated that the pitch of threaded members 164, 166 and 210 (and the inner rod assembly of the handle member, not shown) are not limited to the described embodiments and may have any size pitch and formed in any suitable manner understood by the skilled artisan.

In view of the foregoing, the present disclosure, through one or more of its various aspects, embodiments and/or specific features or sub-components, is thus intended to bring out one or more of the advantages as specifically noted below.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. Additionally, the illustrations are merely representational and may not be drawn to scale. Certain proportions within the illustrations may be exaggerated, while other proportions may be minimized. Accordingly, the disclosure and the figures are to be regarded as illustrative rather than restrictive.

One or more embodiments of the disclosure may be referred to herein, individually and/or collectively, by the term "invention" merely for convenience and without intending to voluntarily limit the scope of this application to any particular invention or inventive concept. Moreover, although specific embodiments have been illustrated and described herein, it should be appreciated that any subsequent arrangement designed to achieve the same or similar purpose may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The Abstract of the Disclosure is provided to comply with 37 C.F.R. §1.72(b) and is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, inventive subject matter may be directed to less than all of the features of any of the disclosed embodiments. Thus, the following claims are incorporated into the Detailed Description, with each claim standing on its own as defining separately claimed subject matter.

The above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. A removable tip for a laparoscopic device, comprising:
    an exposed electrically-conductive outermost casing with a first threaded member and configured as an electrical energy path when the removable tip is attached to the laparoscopic device; and
    an electrically-conductive inner shaft located at least partially within the outermost casing and having a second threaded member, wherein:
    electrical current supplied by a power source is configured to pass though the inner shaft,
    the electrical current is further configured to return from the inner shaft to the power source by passing through the outermost casing as a return path, to complete an electrical circuit,
    and wherein the first threaded member and the second threaded member are mateable with a handle of the laparoscopic device.

2. The removable tip according to claim 1, wherein the first threaded member and the second threaded member are different thread forms and configured to mate with complementing threaded members.

3. The removable tip according to claim 1, further comprising a cutting and sealing instrument at an end of the removable tip opposite of the second threaded member and including at least one resistive heating member.

4. The removable tip according to claim 3, wherein electrical energy is provided to and traversed along a path of the inner shaft of the removable tip, and the electrical energy returns along the electrical energy path defined by the outermost casing.

5. The removable tip according to claim 4, wherein the at least one resistive heating member is activated when provided with the electrical energy.

6. The removable tip according to claim 1, wherein the outermost casing has a detent and is spring biased at the first threaded member end.

7. The removable tip according to claim 1, wherein the first threaded member has a helix angle different from a helix angle of the second threaded member.

8. The removable tip according to claim 1, further comprising insulation located between the inner shaft and the outermost casing, which insulation extends along at least a portion of the length of the outermost casing.

9. The removable tip according to claim 1, wherein the second threaded member comprises a set of threads extending to both inner and outer sides of the first outermost casing.

10. The removable tip according to claim 1, wherein a pitch of inner and outer threads of the first threaded member and the second threaded member are the same.

* * * * *